United States Patent
Hensby et al.

(10) Patent No.: US 9,345,720 B2
(45) Date of Patent: May 24, 2016

(54) COMPOSITION AND METHOD FOR TREATING WOUNDS

(75) Inventors: Christopher N. Hensby, Saint Germain en Laye (FR); Mats Silvander, Uppsala (SE)

(73) Assignee: Exeltis USA Dermatology, Inc., Chatham, NJ (US)

( * ) Notice: Subject to any disclaimer, the term of this patent is extended or adjusted under 35 U.S.C. 154(b) by 23 days.

(21) Appl. No.: 13/204,228

(22) Filed: Aug. 5, 2011

(65) Prior Publication Data

US 2012/0100081 A1   Apr. 26, 2012

Related U.S. Application Data

(60) Provisional application No. 61/406,804, filed on Oct. 26, 2010.

(51) Int. Cl.
| | | |
|---|---|---|
| A61K 31/695 | (2006.01) | |
| A61P 17/02 | (2006.01) | |
| A61P 17/16 | (2006.01) | |
| A61K 9/12 | (2006.01) | |

(52) U.S. Cl.
CPC ............... *A61K 31/695* (2013.01); *A61K 9/12* (2013.01)

(58) Field of Classification Search
CPC .............................. A61K 31/695; A61K 9/12
IPC ............ A61K 31/695, 9/12; A61P 17/02, 17/16
See application file for complete search history.

(56) References Cited

U.S. PATENT DOCUMENTS

| 5,002,938 A | 3/1991 | Wang et al. |
|---|---|---|
| 5,919,470 A | 7/1999 | Valdez et al. |
| 5,993,830 A | 11/1999 | Freij |
| 2004/0241099 A1 | 12/2004 | Popp et al. |
| 2006/0193789 A1 | 8/2006 | Tamarkin et al. |
| 2008/0175793 A1 | 7/2008 | Silvander |
| 2009/0274769 A1* | 11/2009 | Fregonese ............ A61K 31/201 424/537 |
| 2010/0297200 A1* | 11/2010 | Schoenfisch et al. ......... 424/401 |

FOREIGN PATENT DOCUMENTS

| DE | 4207704 | 9/1993 |
|---|---|---|
| DE | 4442561 | 6/1996 |
| WO | WO 98/31339 | 7/1998 |
| WO | WO 02/38160 | 5/2002 |
| WO | WO 03/055454 | 7/2003 |

OTHER PUBLICATIONS

Biafine.TM. Topical Emulsion, Product information sheet, Obtained online. Revised Dec. 2012.*
Burks, Povidone-Iodine solution in wound treatment, Physical Therapy, vol. 78. No. 2, Feb. 1998.*
International Search Report and Written Opinion in PCT/US2011/046793, dated Mar. 28, 2012, 5 pgs.
International Search Report & Written Opinion in PCT/US2011/046785, dated Mar. 9, 2012, 12 pgs.

* cited by examiner

*Primary Examiner* — Mina Haghighatian
(74) *Attorney, Agent, or Firm* — Don J. Pelto, Esq.; Sheppard, Mullin, Richter & Hampton LLP

(57) ABSTRACT

Provided, among other things, is a method of treating a wound comprising: periodically applying to the wound over a course of days an effective amount of a water based formulation (comprising: 0.5 to 5 wt % of an emollient comprising silicone oil, 2 to 10 wt % of fatty acid, humectant(s), emulsifying agent(s), and polymer(s)), wherein the formulation is formulated as a spray, cream, lotion, milk or foam-former.

26 Claims, No Drawings

COMPOSITION AND METHOD FOR TREATING WOUNDS

CROSS-REFERENCE TO RELATED APPLICATION

This application claims the benefit of U.S. Provisional Application No. 61/406,804, filed on Oct. 26, 2010, the content of which is incorporated herein by reference in its entirety.

BACKGROUND OF THE INVENTION

The present invention relates to a water-based composition of silicone oil, fatty acid(s), and humectant(s), which can be used to treat skin and soft tissue wounds, ulcers, burns, various types of dermatoses, inflammatory conditions of the mucosa, and the like.

A foamable composition similar to those described herein is described in U.S. Pat. No. 5,993,830. The composition has been used with subjects having chronic hand eczema. What was not described, and what has now been unexpectedly discovered, is that such compositions can accelerate healing of wounds and control inflammation.

SUMMARY OF THE INVENTION

Provided, in one embodiment, is a method of treating a wound comprising: periodically applying to the wound over a course of days an effective amount of a water based formulation (comprising: 0.5 to 5 wt % of an emollient comprising silicone oil, 2 to 10 wt % of fatty acid, humectant(s), emulsifying agent(s), and polymer(s)), wherein the formulation is formulated as a spray, cream, lotion, milk or foam-former.

Also provided is a method of treating an inflammatory condition of mucosal tissues comprising: periodically applying to the inflammatory condition over a course of days an effective amount of a water based formulation (comprising: 0.5 to 5 wt % of an emollient comprising silicone oil, 2 to 10 wt % of fatty acid, humectant(s), emulsifying agent(s), and polymer(s)), wherein the formulation is formulated as a spray, cream, lotion, milk or foam-former.

Further provided is a method of treating a dermatoses comprising: periodically applying to the dermatitis over a course of days an effective amount of a water based formulation (comprising: 0.5 to 5 wt % of an emollient comprising silicone oil, 2 to 10 wt % of fatty acid, humectant(s), emulsifying agent(s), and polymer(s)), wherein the formulation is formulated as a spray, cream, lotion, milk or foam-former.

Additionally provided is a formulation comprising: 0.5 to 5 wt % of an emollient comprising silicone oil, 2 to 10 wt % of fatty acid, 0.25% to 4% alkyl pyridinium chloride surfactant, humectant(s), emulsifying agent(s), and polymer(s); wherein the formulation is formulated as a spray, cream, lotion, milk or foam-former.

Further provided is a method of reducing the risk of infection from a skin or mucosa piercing procedure comprising: applying to the skin or mucosa to be pierced an effective amount of a water based formulation (comprising: 0.5 to 5 wt % of an emollient comprising silicone oil, 2 to 10 wt % of fatty acid, humectant(s), emulsifying agent(s), and polymer(s)), wherein the formulation is formulated as a spray, cream, lotion, milk or foam-former; and piercing the skin or mucosa.

DETAILED DESCRIPTION OF THE INVENTION

In certain embodiments, the formulation of the invention provides a non-irritating composition. Irritation, in certain embodiments, is measured by ISO 10993-10: 2002 Standard, "Biological Evaluation of Medical Devices, Part 10-Tests for Irritation and Sensitization," pp. 6-10, 21, which testing method is incorporated herein by reference. In particular, for each test site on shaved dorsal skin of an albino rabbit, gauze incorporating 0.5 mL of test material or negative control material is applied. One test and one control site are used on each side of the paravertebral skin. The infused gauzes are covered with tape-backed gauze. The trunk of the rabbit is wrapped in elastic bandage secured by hypoallergenic tape. After a minimum of 24 hours, the coverings are unwrapped. Observations are made at 60 min±2, 24 h±2, 48 h±2 and 72 h±2 post unwrapping. Tissue reactions are rated for gross evidence of erythema and edema.

For a given rabbit, values for each test site and each of the 24 h, 48 h and 72 h measurements are totaled, and divided by six (2 tests sites×3 measurements). Control values were treated in the same way. For all rabbits, these test values were summed, normalized against the summed values for the negative controls, and divided by the number of animals. A negligible, slight, moderate or severe response is categorized based on the Primary Irritation Index:

| Response Category | Comparative Mean Score |
|---|---|
| Negligible | 0 to 0.4 |
| Slight | 0.5 to 1.9 |
| Moderate | 2 to 4.9 |
| Severe | 5 to 8 |

By "non-irritating" it is meant that compositions according to this embodiment of the invention elicit a negligible Primary Irritation Index.

The non-irritating quality of these embodiments is surprising in view of the surfactants often found in these embodiments. While not being bound by theory, it is believed that water and appropriate selection of relatively mild surfactants, as illustrated herein, may contribute to the non-irritating quality of the wound-treating composition.

Irritation, in certain embodiments, is measured by the 21-Day Cumulative Irritation procedure, originally introduced by Lanman et al. (Joint Conference on Cosmetic Sciences, the Toilet Goods Association (now named The Cosmetic, Toiletry and Fragrances Association) Wash. D.C., Apr. 21-23, 1968), that has been successfully employed as a test for comparing the irritation potential of mild to moderately irritating topically applied skin care products. The procedure involves daily consecutive applications of occlusive patches to human skin over a 21-Day period. Each of the patches applied is worn for approximately 24 hours, removed under supervision and the sites scored by a trained evaluator.

The relative cumulative irritation potential of topically applied test articles can be compared to a negative (Johnson's® Baby Oil) and a positive (0.2% v/v sodium lauryl sulfate) control following repetitive daily applications to the skin of normal, healthy adult volunteers. The test articles, in addition to Johnson's® Baby Oil and 0.2% sodium lauryl sulfate (v/v in DI water) are rubbed in to the upper back between the left and right infra-scapular areas and then covered with a blank semi-occlusive patch. Test article application sites are randomized to limit site bias. Products are rubbed in and blank semi-occlusive patches were applied to the same sites every day for twenty-one (21) consecutive days for a total of 21 applications. Each patch is worn for approximately 24 hours, removed under clinical supervision and the test sites evaluated approximately 10 minutes following patch removal. If a dermal reaction of a 3-level or greater occurs with any of the test articles at any point during the study, further patch testing on that subject at the test site involved is terminated and the observed score is assigned to that site for all remaining scheduled test days (i.e., last score observed carried forward). If a test site is discontinued for reasons other than a dermal reaction of a 3-level or greater (due to erosion, scabbing, etc.), an erythema score of 3 and any other alpha character associated with the score is imputed and assigned to that site for all remaining scheduled test days. If a test subject exhibits a significant degree of irritation to the adhesive such that patch reapplication is not feasible, the test subject is discontinued from the study and the scores for this subject were not used in determining the cumulative irritation totals. When warranted, individual sites are discontinued due to tape reaction (i.e., tape dermatitis) and are not used in determining the cumulative irritation totals. Individual test article scores are calculated via summation of the results for each day. Subjects receive 21 rub-in applications of 0.2 mL of the test articles (including controls) to both sides of their back during the course of the study. Total cumulative irritation scores are determined for each test article by summing the daily erythema scores for each subject.

In certain embodiments, the wound-treating composition of the invention has a "non-greasy feel" when applied. A non-greasy feel is measured in reference to a comparison of the feel of the Example 1 composition (non-greasy standard) of U.S. application Ser. No. 12/016,371, filed Jan. 18, 2008 (US2008/175793), applied to skin at 1 mg/cm$^2$, compared to the oil-based product described in the Table at Column 3 of U.S. Pat. No. 5,919,470 (Bradley Pharmaceuticals, Inc., greasy standard), applied in the same amount. Application includes working the wound-treating composition into the skin. While the feel of compositions of the invention may vary, in making the comparison between the non-greasy standard, the greasy standard, and the prospective non-greasy composition, it will be apparent which category the prospective composition falls within. The non-greasy skin feel may be moist and smooth feeling, but the difference in greasy feel relative to the greasy comparative shall be clear.

In certain embodiments, the wound-treating composition of the invention has a "non-watery feel" when applied. A non-watery feel is a feel much like that of the Example 1 composition (non-watery standard) of U.S. application Ser. No. 12/016,371, filed Jan. 18, 2008 (US2008/175793), applied to skin at 1 mg/cm$^2$. A feel that, in contrast, is noticeably more watery is disqualified.

In certain embodiments, the formulation of the invention provides a non-sensitizing composition. Sensitization, in certain embodiments, is measured by ISO 10993-10: 2002 Standard, "Biological Evaluation of Medical Devices, Part 10-Tests for Irritation and Sensitization," pp. 6-10, 21, which testing method is incorporated herein by reference. Dermal sensitization testing for topical products places into different categories based on their potential to cause dermal sensitization in guinea pigs and extrapolating the results to humans.

In the Induction Phase, ten test guinea pigs are patched with a composition of the invention and 5 guinea pigs are patched with the negative control article, removed after at least 6 hour exposure. After a 24-hour rest period, each site was observed for erythema and edema. The procedure is repeated 3 times per week for 3 weeks. In the Challenge Phase, following a 2 week rest period, the animals are topically patched again, removed after at least 6 hours of exposure. Dermal patch sites are observed for erythema and edema 24 and 48 hours after patch removal. Each animal is assessed for a sensitization response and test results were based upon incidence and severity of the sensitization reaction.

Certain embodiments involve the treatment of "partial thickness wounds," which for the purposes of this application are those that involve the epidermis and at least a portion of the dermis. Wound healing is measured in the pig model by International Standards Organization (ISO) Guidelines 10993-1 (2003), 10993-2 (2006), 10993-4 (2002), and/or 10993-6 (2007). This kind of study is conducted to determine the effects compositions of the invention applied topically on wound healing in a split thickness skin graft model in the pig. Domestic Yorkshire crossbred swine undergo a single surgical procedure during which six split thickness skin graft wounds were created using a dermatome on the dorsum, three wounds on either side of the dorsal midline. Each site is treated with one of three treatments, Standard Care Dressing (non-adherent absorbable dressing, Johnson & Johnson), Positive Control 1 (Biafine Ointment), or the Test Article (ProDerm—Hydrometic Foam). The topical treatments are applied topically to wound sites once daily for 14 days at a dose volume of approximately 4 mg/cm$^2$ (approximately 25 mg). Observations for morbidity, mortality, injury, and the availability of food and water are conducted, for example, twice daily. Clinical observations are for example conducted weekly. Body weights are measured and recorded pretest and (for example) weekly. Physical examinations are conducted pretest. Blood samples for clinical pathology evaluations are collected from all animals pretest. Wound sites of all animals are evaluated for healing and photographs were obtained from all animals on Days 1 (evaluation only), 4, 7, 10 and 14. Wound measurements are performed in the wound area for all animals on Days 4, 7, 10, and 14. At study termination, complete necropsy examinations are performed and selected tissues were microscopically examined.

In certain embodiments, the formulation of the invention is non-comedogenic where the method of measuring comedogenicity is a modification of that described by Dr. Otto Mills (Mills et al., Archives of Dermatology 118: 903-905, 1982). For example, one of the compositions of Table A (described below) was tested using this model. Testing can be, for example, in a single center, test site randomized study comparing the ability of the composition to induce microcomedone formation relative to a•positive (Acetulan™) and a negative (Blank Patch) control. Approximately 0.2 mL of the composition and the positive control are applied to blank semi-occlusive patches (TruMed™ patches containing needle punch absorbent cotton and Alpharma Scantape, Brady Medical, Mesquite, Tex.) and these patches, along with a negative control (blank semi-occlusive patch), are applied to the upper back between the left and right infra-scapular areas. Patch application sites are randomized as to their position on the subjects' backs to eliminate test site bias. Patches are applied three times a week (e.g., every Monday, Wednesday and Friday) for twelve patch applications (i.e., 4 weeks) to the designated test sites. Subjects are instructed to wear the patches continuously for 48 hours following the first and second weekly patch applications and continuously for 72 hours after the third patch application. The sites were scored for the presence of erythema according to an agreed upon scale.

At the final visit, after all patches are removed and the test sites are scored for erythema, follicular biopsies of the sites were collected using a cyanoacrylate follicular biopsy technique. Follicular biopsies are examined under a stereo microscope and the number of microcomedones present on the slides counted. The number of microcomedones present at the treated test sites are compared to that observed for the positive and negative control sites to determine significance. The negative control should significantly less microcomedones than the positive control to a high statistical confidence (e.g., $P \leq 0.05$). Where the number of microcomedones at the sites treated with the test composition are not significantly different from the number of microcomedones observed at the negative control sites, the test composition is "non-comedogenic."

The compositions of the invention can be used to treat dermatoses (inflamed skin) and skin wounds. For the purposes of the claims, "dermatoses" that can be treated with the compositions of the invention can either be an acute or a chronic inflammatory condition of the skin including atopic dermatitis or radiation dermatitis. For this purpose, eczema, irritant contact dermatitis and allergic contact dermatitis are not a dermatoses. For the purposes of the claims, a "wound" that can be treated with the compositions of the invention is an acute or chronic partial or full thickness skin or soft tissue wound including incisions, abrasions, lacerations, penetration wounds, burns, ulcerations, and surgical wounds.

Mucosal tissues that are candidates for treatment include, for example, esophageal mucosa, rectal mucosa, anal mucosa, urethral mucosa, vaginal mucosa, external mucosa, oral mucosa, and the like. Inflammatory conditions of mucosal tissues can be treated with the compositions of the invention. Such conditions include, for example, gingivitis, mucositis (including as a consequence of chemotherapy or radiotherapy), anal fissures, and the like.

To treat the wound indications of the invention, an "effective amount" of the composition will be recognized by clinicians but for wounds includes an amount effective to accelerate healing to a degree comparable to Biafine Ointment. In certain embodiments for treating wounds, the effective amount is effective to accelerate healing to a degree superior to Biafine Ointment. To treat the mucosal indications of the invention, an "effective amount" of the composition will be recognized by clinicians but includes an amount effective to treat, reduce, alleviate, ameliorate, eliminate or prevent one or more symptoms of the disease sought to be treated or the condition sought to be avoided or treated, or to otherwise produce a clinically recognizable favorable change in the pathology of the disease or condition. To treat the dermatoses (e.g. dermatitides) of the invention, an "effective amount" of the composition will be recognized by clinicians but includes an amount effective to treat, reduce, alleviate, ameliorate, eliminate or prevent one or more symptoms of the disease sought to be treated or the condition sought to be avoided or treated, or to otherwise produce a clinically recognizable favorable change in the pathology of the disease or condition. In all treatments, an effective amount can be effective to accelerate reduction in symptoms to a degree comparable to, or superior to, Biafine Ointment.

Generally, the formulation of the invention is applied two to three times a day to the affected tissue, in amounts of 1 to 5 mg/cm$^2$, or as needed or prescribed.

For certain indications of the mucosa, the foam or gel form may often be selected due to the greater ease in assuring coverage of the affected tissue.

In certain embodiments using the foam form, the foam is a stable foam, meaning that when applied to the skin at one of 1, 2 or 3 mg/cm$^2$ and not worked into the skin, the foam remains a stably adherent foam for 30 seconds or more. In some cases, the foam remains a stably adherent foam for 60 seconds or more, 120 seconds or more, 150 seconds or more or 180 seconds or more. Though stable, the foam can be worked into the patient's skin.

In certain embodiments, the wound-treating composition of the invention is essentially free of C1 to C6 alcohols (but not including polyols, such as glycerin or propylene glycol). In certain embodiments, the wound-treating composition is essentially free of C1 to C5 alcohols (but not including polyols, such as glycerin or propylene glycol). In certain embodiments, the wound-treating composition is essentially free of C1 to C4 alcohols (but not including polyols, such as glycerin or propylene glycol). By essentially free it is meant that such alcohols may be present in minor amounts, as may be useful for example for compounding, but are not present in an amount that one of skill in the art of pharmaceutical wound-treating composition formulating would select to stabilize components of the composition. In these embodiments, the amount of such alcohols is less than about 8 wt %. In certain embodiments, the amount of such alcohols is less than about 5%, or 2%, or 1%, or 0.5%, or 0.25% (wt/wt).

When worked into the skin, the compositions of the invention can have rapid absorption—contributing to their non-greasy and non-watery feels. The compositions can be easy to spread and are cosmetically elegant.

While the wound-treating compositions can contain active ingredients, such as antimicrobial agents, surprisingly the wound treating efficacy can be obtained without such agents, using only components that are not traditionally regarded as active ingredients. While not being bound by theory, it is believed that this efficacy is due to (a) physically providing a protective artificial barrier on the affected surface; (b) providing moisture to the skin/mucosa and improving its hydration; and (c) effectively controlling the inflammation in the affected area.

The composition contains fatty acids, which can be substantially or essentially ionized, wherein the salt may be more soluble or suspendable in the aqueous solvent of the composition. The fatty acids are, in certain embodiments, non-greasy, meaning that in the aggregate of the formulation, as formulated in the wound-treating composition, they are non-greasy.

The fatty acid can, for example, be of any composition found in a natural source, including hydrolysis of esterified fatty acids. Or, the fatty acid component can be hydrogenated to remove substantially all or a portion of any unsaturation. In certain embodiments, the fatty acid component is selected such that 50 mole % or more is C12 or higher, or C14, or C16 or higher. In certain embodiments, the fatty acid component is selected such that 50 mole % or more is C22 or lower, or C20 or lower, or C18 or lower. In certain embodiments, 75 mole % or more of the fatty acid component is from C12 or C14 or C16 to C22 or C20 or C18. In certain embodiments, 80 mole % or more, 85 mole % or more, 90 mole % or more, 95 mole % or more, 97 mole % or more, 98 mole % or more, or 99 mole % or more, meets one of the size parameters of this paragraph.

Useful salts of the fatty acids include the alkali metal salts such as sodium or potassium salts; ammonium salts; salts formed with suitable organic bases, such as amine salts (such as triethyl amine, triethanol amine, or the like) and quaternary ammonium salts; or the like. Bivalent or trivalent salts can be used where they do not adversely affect solubility. As needed, the fatty acid components are provided such that a sufficient amount of constituent ionizable molecules are in ionized (salt) form to provide solubility. Such ionized forms can be prepared by adding a titrant. Recitations of compositions described by their formation by titration include the equivalent compositions formed by pre-formed salts or otherwise.

In certain embodiments, the fatty acid(s) comprise an amount of E or more, F or less, of from E to F of the wound-treating composition, where E is 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, 5, 5.1, 5.2, 5.3, 5.4, 5.5, 5.6, 5.7, 5.8, 5.9 or 6 wt %, and F is 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, 5, 5.1, 5.2, 5.3, 5.4, 5.5, 5.6, 5.7, 5.8, 5.9, 6, 6.1, 6.2, 6.3, 6.4, 6.5, 6.6, 6.7, 6.8, 6.9, 7, 7.1, 7.2, 7.3, 7.4, 7.5, 7.6, 7.7, 7.8, 7.9, 8. 8.1, 8.2, 8.3, 8.4, 8.5, 8.6, 8.7, 8.8, 8.9, 9, 9.1, 9.2, 9.3, 9.4, 9.5, 9.6, 9.7, 9.8, 9.9 or 10 wt %. Unless otherwise specified, the composition percentages for the wound-treating compositions are exclusive of any propellant, such as propane or butane or the like.

An emollient, if present, can be a silicone oil such as polydimethylsiloxane (i.e., dimethicone), petrolatum (natural or synthetic), or the like. In certain embodiments, the emollient(s) are an amount I or more, J or less, or I to J of the wound-treating composition, where I is 0.5, 0.6, 0.7, 0.8, 0.9, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9 or 4 wt %, and J is 0.6, 0.7, 0.8, 0.9, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9 or 5 wt %. In certain embodiments, as among emollients and fatty acids in the wound-treating composition, the amount of emollient is an amount K or more, L or less, or K to L of the emollients and fatty acids, where K is 5, 6, 7, 8, 9, 10, 11, 12, 13, 14, 15, 16, 17, 18, 19 or 20 wt %, and L is 6, 7, 8, 9, 10, 11, 12, 13, 14, 15, 16, 17, 18, 19, 20, 21, 22, 23, 24 or 25 wt %. Relative amounts of any petrolatum can be selected to minimize comedogenicity. In certain embodiments, silicone oil is a major portion of the emollient component by weight. In certain embodiments, silicone oil is 80, 85, 90, 95, 96, 97, 98, 99, 99.5% or more of the emollient component (by weight).

The wound-treating composition will typically include emulsifying agents. Emulsifying agents can be non-ionic detergents, such as polyoxyethylene sorbitan fatty acid esters (such as Tween 80 (polyoxyethylene (20) sorbitan monolaurate), Polysorbate 20 (polyoxyethylene (20) sorbitan monooleate)), sorbitol fatty acid esters, octyly glucosides, PEGylated lipids and the like. In certain embodiments, the emulsifying agent(s) comprise an amount of M or more, N or less, of from M to N of the wound-treating composition, where L is 0.5, 0.6, 0.7, 0.8, 0.9, 2, 1.1, 1.2, 1.3, 1.4, 1.5, 1.6, 1.7, 1.8, 1.9 or 2 wt %, and N is 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9 or 4 wt %. The emulsifying agent(s) can comprise detergents with 2 or more, 3 or more, 4 or more, 5 or more fold difference in CMC. The emulsifying agents can, for example, have a CMC at 21° C. of $2\times10^{-6}$M to $10^{-4}$M. In certain embodiments, where there are two or more frothing agents, the predominant (by wt) frothing agent can have the lower CMC vs the next most predominant frothing agent.

Hydrophilic polymer(s) can be present. These can be any non-toxic water soluble polymer(s) that (in the aggregate) stabilize wound-treating composition and contribute to film formation on the skin. Examples include polyvinyl pyrrolidone, polyethylene glycol, starch, water-soluble derivatives of starch, cellulose, methyl cellulose, hydroxymethylcellulose, other water-soluble derivatives of cellulose, carbomers, or the like. For polyvinyl pyrrolidone, for example, useful average molecular weights include from 8,000 to 63,000, such as about 38,000. For all polymers used in the composition, the size can be sufficient to limit penetration of the horny layer of the skin, if skin penetration is an issue for the given polymer. In certain embodiments, hydrophilic polymer(s) are an amount I or more, J or less, or I to J of the wound-treating composition.

The composition can also contain a humectant, such as glycerol, propylene glycol, other polyols, polydextrose, lactic acid, or the like. In certain embodiments, humectant(s) are an amount O or more, P or less, or O to P of the wound-treating composition, where O is 4, 4.1, 4.2, 4.3, 4.4, 4.5, 4.6, 4.7, 4.8, 4.9, 5, 5.1, 5.2, 5.3, 5.4, 5.5, 5.6, 5.7, 5.8, 5.9, 6, 6.1, 6.2, 6.3, 6.4, 6.5, 6.6, 6.7, 6.8, 6.9, 7, 7.1, 7.2, 7.3, 7.4, 7.5, 7.6, 7.7, 7.8, 7.9 or 8 wt %, and P is 5, 5.1, 5.2, 5.3, 5.4, 5.5, 5.6, 5.7, 5.8, 5.9, 6, 6.1, 6.2, 6.3, 6.4, 6.5, 6.6, 6.7, 6.8, 6.9, 7, 7.1, 7.2, 7.3, 7.4, 7.5, 7.6, 7.7, 7.8, 7.9, 8, 8.1, 8.2, 8.3, 8.4, 8.5, 8.6, 8.7, 8.8, 8.9, 9, 9.1, 9.2, 9.3, 9.4, 9.5, 9.6, 9.7, 9.8, 9.9, 10, 10.1, 10.2, 10.3, 10.4, 10.5, 10.6, 10.7, 10.8, 10.9, 11, 11.1, 11.2, 11.3, 11.4, 11.5, 11.6, 11.7, 11.8, 11.9 or 12 wt %.

The wound-treating composition can optionally contain a preservative or preservative system. Examples include Phenonip™ XB (a mixture of preservatives, believed to include phenoxyethanol, methylparaben, ethylparaben, butylparaben, propylparaben and isobutylparaben; from Clariant UK Ltd., Leeds, UK), or a less complex preservative, such as one or two of methylparaben, ethylparaben, butylparaben, propylparaben, isobutylparaben, benzalkonium chloride, imidurea or the like.

The wound-treating compositions will typically contain titrating agents such as trolamine, NaOH, citrate, phosphates, and the like. The amount is typically selected to provide a dermatologically or physiologically acceptable pH, such as pH 4-9, or 5-9, or 6-9.

The wound-treating compositions can be formulated as sprays, creams, lotions, milks, foam-formers, and the like. Where creams or lotions are desired, these consistencies can be obtained by selection of hydrophilic polymers, and the amounts thereof. For example, these can include polymers that have a greater effect on increasing viscosity, in appropriate amounts. Such polymers can include, for example, appropriate carbomers, carbopols, methylcellulose, hydroxyethyl cellulose, hydroxyethylmethyl cellulose, hydroxypropyl cellulose, polyvinyl pyrrolidone, hypromellose, polyethylene glycol, polyethylene oxide, xanthan gum, Arabic gum, pectin, starch, alginate and the like. Addition of suitable hydrophilic co-polymer permits the formation of different forms that retain the same safety and efficacy properties as the foam-forming formulations but do not require the use of gaseous propellants for their delivery to the treatment area. In such embodiments, it may be that the amounts of polymer are to the high end or greater than those amounts discussed above.

Suitable propellants include, for example, propane, butane, isobutene, other hydrocarbons, hydrofluorocarbons, chlorofluorocarbons (Cl/F/(H)/C), and the like. Dispensing devices include those available from Deutsche Präzision, Lindal Group (Schönberg, Germany), Coster (Milano, Italy) and SeaquistPerfect Dispensing (Cary, Ill.).

The formulation of the invention is, in certain embodiments, a stable emulsion. In others, the formulation provides an emulsion when shaken/agitated prior to use. For certain of the foam embodiments, the formulation should be shaken/agitated prior to use. Certain foam embodiments provide a foam that is relatively stable at 35° C., such as stable for 1 or more minutes, or 2 or more minutes, or 3 or more minutes, a period of time allowing for convenient transfer of the foam from a gloved or naked hand to the tissue to be treated. In certain embodiments, including certain thermally stable embodiments, the foam breaks, i.e., loses its foam texture, on application of the shear used to manually apply the foam to the tissue.

Formulations of the invention have been found to be remarkably antimicrobial. As such, they can be used prepare skin or mucosa for treatments that are skin or mucosa piercing, such as surgery, IVs, needle biopsies, acupuncture, and the like, or for treating wounds or other dermatological conditions complicated by bacterial infection.

For example, forearm areas were treated with formulation for 5, 10, 20 or 40 minutes, then challenged with ~$10^5$ CFU of *Escherichia coli* (ATCC #11229) or *Staphylococcus aureus aureus* MRSA (ATCC #33593). Microbial colonization was inhibited to a statistically significant extent after 10 minutes exposure or more for *Staph. aureus* MRSA, and after 20 minutes or more for *E. coli*.

In certain embodiments, the formulation can contain an alkyl pyridinium chloride surfactant, such as cetylpyridinium chloride. The amount can, for example, be 0.25% wt or more, or 0.3, 0.4, 0.5, 0.6, 0.7, 0.8, 0.9 or 1% wt or more. The amount can, for example, be 4% wt or less, or 3.5, 3.0, 2.5, 2.0, 1.5, 1.3, 1.2, 1.1, 1.0, 0.9, 0.8, 0.7, 0.6 or 0.5% wt or less. Various antimicrobial agents can be further added.

In certain embodiments, the compositions used in the methods of the invention lack any antimicrobial compounds, where the emollient, fatty acid, humectant and emulsifying agents are present in amounts appropriate to provide skin moisturization, skin barrier repair (fatty acid), and the texture properties desired (spray, cream, and the like). In certain embodiments, the emollient, fatty acid, humectant and emulsifying agents are present in amounts appropriate to provide one or more of non-irritation, non-sensitization or non-comedogenicity. In certain embodiments, the emulsifying agent consists essential of (no other present in amounts beyond minor amounts such as 0.1% by wt used to facilitate making intermediate formulations used in the formulation process) nonionic detergent(s). The nonionic detergents can be those where polyoxyethylene and or sugar moieties provide the hydrophilic portion, and hydrocarbons (e.g., alkanyl or alkenyl) provide the hydrophobic portion. In certain embodiments, the compositions used in the methods of the invention lack any antimicrobial compounds other than an alkyl pyridinium chloride surfactant, where the emollient, fatty acid, humectant and emulsifying agents are present in amounts appropriate to provide skin moisturization, skin barrier repair (fatty acid), and the texture properties desired (spray, cream, and the like).

One can test antimicrobial effect in an in vitro time kill method, such as by mixing 0.1 mL challenge bacterial suspension with 9.9 g of test product. After one minute, 1.0 mL of the mix is added to 9.0 mL of Butterfield's Phosphate Buffer, with neutralizers where applicable. Serial dilutions into the same buffer are plated onto Tryptic Soy agar plates.

To formulate 100 g, one can for example formulate all or a selection of the formulations defined by the combinations of the following options:

TABLE A

| | Component | Amt. Options (g) |
|---|---|---|
| A1 | Water | Quantity sufficient |
| A2 | Povidone | 1-3 |
| A3 | Stearic acid | 5-8 |
| A4 | Propylene glycol | 4-7 |
| A5 | Glycerol | 1-2 |
| A6 | Dimethicon | 0.5-5 |
| A7 | Triethanol amine | 0-3 |
| A8 | Polysorbate 20 | 1.3-5.0 |
| A9 | Preservative | 0-2.0 |

The above can be formulated by heating A1 and adding stepwise A2-A9 while stirring. When homogeneous the formulation is cooled to room temperature or similar and formulations can be tested for foam forming (if appropriate), foam stability (if appropriate), non-wet feel, irritation, non-greasy feel, and the like.

In another embodiment, to formulate 100 g, one can for example formulate all or a selection of the formulations defined by the combinations of the following options:

TABLE B

| | Component | Amt. Options (g) |
|---|---|---|
| C1 | Povidone or thickening agent | 0-3 |
| C2 | Polysorbate 20 | 1.3-5.0 |
| C4 | Stearic acid | 2-10 |
| C5 | Sodium citrate | 0-3 |
| C6 | Glycerol | 1-2 |
| C7 | Triethanol amine | 0-3 |
| C8 | Preservative | 0-2 |
| B | NaOH | 0-1 |
| D | Povidone or thickening agent | 0-3 |
| A2 | Dimethicon | 0.5-5 |
| A1 | Propylene glycol | 4-7 |
| A3 | Tween 80 | 0-5 |
| A4 | Polysorbat 20 | 0.5-5 |
| | Water | Quantity Sufficient |

The above can be formulated in 4 phases: mixing the A components; mixing B in a minor amount of the water; mixing D in a minor amount of the water, mixing the C components in the bulk of the water; adding the mixed A components to the mixed C components; and adding the mixed B components and finally the mixed D components. The A components can be added to A1 stepwise in the order A2 to A4. The C components can be added to water stepwise in the order C1 to C8, with the water heated to promote mixing and solubilization. The mixed B components can be added to heated mixed C components. The mixed A components can be added in parts to the mixed C components, such as after the mixed A components have cooled, but still have an elevated temperature (over r.t.). The mixed D components are added (to A+B) after further cooling. The formulations can be tested for foam forming (if appropriate), foam stability (if appropriate), non-wet feel, irritation, non-greasy feel, and the like.

In certain embodiments, a further thickening agent (e.g., the hydrophilic polymers discussed above) can be added in order to create a gel, cream or a lotion. The above can be formulated in 2 phases: mixing the B component in a minor amount of the water separately. The A components are added to the rest of the heated water stepwise during stirring. Where appropriate a pH adjustment can be made to the phase by use of acid or base. The A phase and the B phase are mixed at the last step and the formulation cooled to ambient.

TABLE C

| | Component | Amt. Options (g) |
|---|---|---|
| B1 | Thickener 1 | 0.05-2.0 |
| A1 | Thickener 2 | 1-3 |
| A2 | Stearic acid | 5-8 |
| A3 | Propylene glycol | 4-7 |
| A4 | Glycerol | 1-2 |
| A5 | Dimethicon | 0.5-5 |
| A6 | Triethanol amine | 0-3 |
| A7 | Polysorbate 20 | 1.3-5.0 |
| A8 | Preservative | 0-2.0 |
| A9 | Water | Quantity sufficient |

EXAMPLES

Example 1

Wound Care

One of the compositions of Table A was tested in a wound treatment model. This composition is designated Test Article in the text below.

Animal Care

Experimentally naive female Domestic Yorkshire crossbred swine, at least 9 weeks of age at receipt, were used. The animals were originally received from Whiteshire Hamroc, Albion, Ind. Prior to use in the study, the animals were weighed weekly and observed with respect to general health and any signs of disease. Ova and parasite evaluations on stool samples were performed, and all results were negative for animals placed in the study.

The animals were individually housed in runs with raised flooring. This type of housing provided adequate room for exercise for these animals. Fluorescent lighting was provided for approximately 12 hours per day. Temperature and humidity were continuously monitored and recorded. The protocol-designated ranges were 61 to 81° F. and 30 to 70%, respectively. Diet (Certified Lab Diet® #5K99, PMI Nutrition International, Inc.) was offered via limited feedings, except during designated periods. Tap water was available ad libitum via an automatic watering system.

Wounding Procedure

The animals were fasted overnight prior to surgery and treated as specified in Table C. Prior to surgery, the appropriate drugs were administered and general anesthesia was induced. A cuffed endotracheal tube was placed and general anesthesia was maintained with isoflurane delivered in oxygen through a rebreathing system with ventilator assist.

TABLE C

Procedure-related Medications and Dose Levels

| Medication | Interval. Dose Level. and Route | |
|---|---|---|
| | Surgery (Day 0) | Daily Postsurgery |
| Acepromazine maleate | 0.1 mg/kg IM | — |
| Atropine sulfate | 0.05 mg/kg IM | — |
| Telazol | 5 mg/kg IM | — |
| Isoflurane | To effect, inhalation | — |
| Buprenorphine | 0.02 mg/kg IM | 0.01 mg/kg IM TID × 3 days |
| Cefazolin | 25 mg/kg IV | — |
| Ceftiofur | 2.2 mg/kg IM | 2.2 mg/kg IM SID × 5 days |
| Lactated Ringer's Solution (LRS) | 5 to 6 mL/kg/hour IV | — |

IM—Intramuscular
IV—Intravenous
TID—Three times daily
SID—Once daily

All surgical procedures were performed utilizing routine aseptic technique. Following induction of anesthesia, the entire dorsal surface was prepared for surgery with Iodine Scrub, 70% isopropyl alcohol, and Iodine solution.

Following completion of preoperative procedures on Day 0, six 2.5 cm×2.5 cm wound sites were marked out, three on either side of the dorsal midline caudal to the scapula and 2.5 cm (animal numbers 101 and 102) or 5 cm (animal numbers 103 and 104) from the midline, using sterile skin marker pens. The wounds were separated from each other (approximately 5 cm) to avoid wound to wound contact. To avoid cross-contamination of Test Article treated wounds with wound treated by Positive Control Article (Biafine Ointment, Ortho-Neutrogena) [purified water, liquid paraffin, ethylene glycol monostearate, stearic acid, propylene glycol, paraffin wax, squalene, avocado oil, trolamine sodium alginate, cetyl palmitate, methylparaben (sodium salt), sorbic acid (potassium salt), propylparaben (sodium salt) and fragrance] and Standard Care (RELEASE® non-adherent absorbable dressing, Johnson & Johnson), the Standard Care wound sites were wounded first, followed by the Positive Control Article wounds and then Test Article. The skin covering the wound site and the dermatome-was moistened with sterile saline using sterile gauze immediately prior to each wound to aid the running of the dermatome. Six 2.5 cm×2.5 cm×0.50 mm (length×width×depth) split thickness skin graft wounds were created using the dermatome; three wounds were created on each side of the dorsal midline.

If necessary, a pair of scissors was used to aid in the removal of skin. The portion of the dermatome in contact with the skin was frequently cleaned with chlorhexadine, and then rinsed with sterile saline. The dermatome blade was changed following completion of the wounding in each pig, prior to commencement of wounding the subsequent pig. Following the completion of wounding, a piece of dry sterile gauze was placed on each wound to absorb excess blood. Following removal of the sterile gauze the appropriate treatment was applied to the wound. The Positive Control and Test Article were applied to each designated wound site by spreading evenly with a sterile spatula (dose volume of approximately 4 mg/cm$^2$, 25 mg). A piece of non-adherent absorbable dressing (Johnson & Johnson) was placed on each wound. The non-stick dressings on each side of the pig were held in place using a sheet of Bioclusive transparent dressing (Johnson & Johnson). The Bioclusive was carefully placed on the wounds, ensuring that it was not pulled too taught to avoid skin irritation. Care was taken to seal the Bioclusive dressing around the four edges of each non-stick dressing. Following the placement of the Bioclusive dressing, the wounds were dressed with Elastikon® elastic tape (Johnson & Johnson): A Surgilast (Glenwood, Inc., Tenafly, N.J.) equivalent to Surgifix (FRA Production S.p.A., Cisterna D'Asti, Italy) stocking was placed on the body of the animal.

Monitoring was conducted during anesthetic recovery for physiological disturbances including cardiovascular/respiratory depression, hypothermia, and excessive bleeding from the surgical site. The endotracheal tube was removed after the animal regained the swallow reflex. Long-term postoperative monitoring included daily inspection of surgical sites. Medications were administered as presented in Table C.

Wound Administrations

The treatments, Standard Care Dressing (sterile gauze bandage), Positive Control, and Test Article, were administered via topical application to six split thickness skin graft wounds created on the dorsum of the pig. Treatments were administered once daily for 14 days at a dose volume of approximately 4 mg/cm$^2$ (approximately 25 mg). Wounds were randomly treated with each of the three treatments in a manner that allowed each animal to receive two sites treated with each treatment.

On each day of the study (Days 1 to 14), Telazol (5 to 6 mg/kg, IM) was administered and anesthesia was maintained with isoflurane delivered in oxygen. The bandages were then removed. For the Standard Care treated wounds, the Surgifix stocking or equivalent and Elastikon® elastic tape were removed. The Bioclusive transparent dressing and non-adherent absorbable dressing was then removed from the wound. The site was carefully cleaned with sterile saline and gauze.

Following cleaning, a piece of non-adherent absorbable dressing was placed on each wound. The non-stick dressings on each side of the pig were held in place using a sheet of Bioclusive transparent dressing. The Bioclusive was carefully placed on the wounds, ensuring that it was not pulled too taught to avoid skin irritation. Care was taken to seal the Bioclusive dressing around the four edges of each non-stick dressing. Following the placement of the Bioclusive dressing, the wounds were dressed with Elastikon® elastic tape. A Surgifix stocking or equivalent was placed on the body of the animal.

For the Positive Control treated wounds, the Surgifix stocking or equivalent and Elastikon® elastic tape was removed. The Bioclusive transparent dressing and non-adherent absorbable dressing was then removed from the wound. The site was carefully cleaned with sterile saline and gauze to remove any residual material. Following cleaning, the site was dosed and a piece of non-adherent absorbable dressing was placed on each wound. The non-stick dressings on each side of the pig were held in place using a sheet of Bioclusive transparent dressing. The Bioclusive was carefully placed on the wounds, ensuring that it was not pulled too taught to avoid skin irritation. Care was taken to seal the Bioclusive dressing around the four edges of each non-stick dressing. Following the placement of the Bioclusive dressing, the wounds were dressed with Elastikon® elastic tape. A Surgifix stocking or equivalent was placed on the body of the animal.

For the Test Article treated wounds, the Surgifix stocking or equivalent and Elastikon® elastic tape was removed. The Bioclusive transparent dressing and non-adherent absorbable dressing was then removed from the wound. The site was carefully cleaned with sterile saline and gauze to remove any residual material. Following cleaning, the site was dosed and a piece of non-adherent absorbable dressing was placed on each wound. The non-stick dressings on each side of the pig were held in place using a sheet of Bioclusive transparent dressing. The Bioclusive was carefully placed on the wounds, ensuring that it was not pulled too taught to avoid skin irritation. Care was taken to seal the Bioclusive dressing around the four edges of each non-stick dressing. Following the placement of the Bioclusive dressing, the wounds were dressed with Elastikon® elastic tape. A Surgifix stocking or equivalent was placed on the body of the animal.

Erythema and Edema

The wound and skin around the wound was assessed for the presence of erythema and edema. Assessment of erythema and edema was made after the wound had been gently cleaned, if needed, ensuring no damage was caused. Assessment of erythema and edema was graded on the following 5 point scales, according to Draize (Draize J H, Woodard G, Calvery H O. Methods for the study of irritation and toxicity of substances applied topically to the skin and mucous membranes. J Pharmacol Exp Ther 1944; 82:377-390, 1959) 4 point acute dermal irritation scale.

TABLE F

Erythema Formation

| Score | Observation |
|---|---|
| 0 | No erythema |
| 1 | Very slight erythema (barely perceptible) |
| 2 | Well-defined erythema |
| 3 | Moderate to severe erythema |
| 4 | Severe erythema (beet redness) to eschar formation (injuries in depth) |

Maximum possible score = 4

TABLE G

Edema Formation

| Score | Observation |
|---|---|
| 0 | No edema |
| 1 | Very slight edema (barely perceptible) |
| 2 | Slight edema (edges of area well-defined by definite raising) |
| 3 | Moderate edema (raised approximately 1 mm) |
| 4 | Severe edema (raised more than 1 mm and extending beyond area of exposure) |

Maximum possible score = 4

Results were:

TABLE J

Individual Wound Healing Scores: Erythema

| Study Interval (Days) | Score | Standard Care Dressing (n = 8) | Positive Control 1 (n = 8) | Test Article (n = 8) |
|---|---|---|---|---|
| 1 | 0-no erythema | 8 | 7 | 8 |
|   | 1-very slight | 0 | 1 | 0 |
|   | 2-well defined | 0 | 0 | 0 |
| 4 | 0-no erythema | 6 | 5 | 6 |
|   | 1-very slight | 2 | 3 | 1 |
|   | 2-well defined | 0 | 0 | 1 |
| 7 | 0-no erythema | 4 | 7 | 7 |
|   | 1-very slight | 4 | 1 | 1 |
|   | 2-well defined | 0 | 0 | 0 |
| 10 | 0-no erythema | 5 | 5 | 7 |
|   | 1-very slight | 3 | 3 | 1 |
|   | 2-well defined | 0 | 0 | 0 |
| 14 | 0-no erythema | 4 | 5 | 7 |
|   | 1-very slight | 4 | 3 | 1 |
|   | 2-well defined | 0 | 0 | 0 |

No sites were scored greater than 2 and as such the data is not presented in the summary table.

TABLE K

Individual Wound Healing Scores: Edema

| Study Interval (Days) | Score | Standard Care Dressing (n = 8) | Positive Control 1 (n = 8) | Test Article (n = 8) |
|---|---|---|---|---|
| 1 | 0-no edema | 8 | 8 | 8 |
|   | 1-very slight | 0 | 0 | 0 |
| 4 | 0-no edema | 7 | 6 | 5 |
|   | 1-very slight | 1 | 2 | 3 |
| 7 | 0-no edema | 6 | 8 | 8 |
|   | 1-very slight | 2 | 0 | 0 |
| 10 | 0-no edema | 8 | 8 | 8 |
|   | 1-very slight | 0 | 0 | 0 |
| 14 | 0-no edema | 8 | 8 | 8 |
|   | 1-very slight | 0 | 0 | 0 |

No sites were scored greater than 1 and as such the data is not presented in the summary table.

Exudate

The wound and skin around the wound was assessed for the presence of exudate. Assessment of exudate was made after the wound had been gently cleaned, if needed, ensuring no damage was caused to the wound in doing so. Assessments were graded according to the following 5 point scale. The results were:

TABLE L

Individual Wound Healing Scores: Exudate

| Study Interval (Days) | Score | Standard Care Dressing (n = 8) | Positive Control 1 (n = 8) | Test Article (n = 8) |
|---|---|---|---|---|
| 1 | 0-none | 0 | 0 | 0 |
|  | 1-mild | 0 | 1 | 1 |
|  | 2-moderate | 7 | 7 | 7 |
|  | 3-severe | 1 | 0 | 0 |
| 4 | 0-none | 0 | 0 | 0 |
|  | 1-mild | 2 | 2 | 2 |
|  | 2-moderate | 6 | 6 | 5 |
|  | 3-severe | 0 | 0 | 1 |
| 7 | 0-none | 4 | 7 | 8 |
|  | 1-mild | 4 | 1 | 0 |
|  | 2-moderate | 0 | 0 | 0 |
|  | 3-severe | 0 | 0 | 0 |
| 10 | 0-none | 8 | 8 | 8 |
|  | 1-mild | 0 | 0 | 0 |
|  | 2-moderate | 0 | 0 | 0 |
|  | 3-severe | 0 | 0 | 0 |
| 14 | 0-none | 8 | 8 | 8 |
|  | 1-mild | 0 | 0 | 0 |
|  | 2-moderate | 0 | 0 | 0 |
|  | 3-severe | 0 | 0 | 0 |

No sites were scored greater than 3 and as such the data is not presented in the summary table.

Wound Size

Digital photographs of the site of surgery were taken on Days 4, 7, 10, and 14 during dressing changes and prior to necropsy. Photographs were taken after dressings had been removed and the wound had been gently cleaned, if needed, ensuring no damage was cause to the wound in doing so. For all photographs, a measurement scale was place in the same plane as the surgical sites. Morphometry was performed in the wound area to document changes in wound size. Morphometry was used to determine advancement of wound edge, reduction in total area/percent closure, and time to complete healing.

On Days 4, 7, 10, and 14, digital photos were taken of each wound and the wound area was measured by tracing the edge of the wound. When the wound was considered to be completely healed, the area measurement was 0. The results were:

TABLE M

Average Wound Area (mm$^2$)

| Treatment |  | Day 4 | Day 7 | Day 10 | Day 14 |
|---|---|---|---|---|---|
| Standard Care | Mean Area | 590.1 | 177.6 | 115.5 | 0.0 |
|  | SD | 39.93 | 232.11 | 135.17 | 0.00 |
| Positive Control | Mean Area | 616.4 | 44.3 | 87.7 | 0.0 |
|  | SD | 45.48 | 101.97 | 165.58 | 0.00 |
| Test Article | Mean Area | 632.2 | 18.8 | 0.0 | 0.0 |
|  | SD | 57.00 | 39.00 | 0.00 | 0.00 |

The results of this study demonstrate that application of the Test Article (a cream according to the invention) daily to a split thickness skin graft wound in the pig does not adversely affect wound healing. Application of the Test Article was found to reduce the incidence of localized erythema and reduce the amount of time that exudate was present at the site of injury. When evaluated for time to complete closure of the wound, application of the Test Article was found to accelerate healing. Wounds treated with the test article achieved complete closure by Day 7-10 post injury, whereas wounds treated with the standard of care required 10-14 days. At 7 days, wounds treated with the positive control article appeared to be healing at the same rate as wounds treated with the Test Article. By Day 10, three of these wounds had reopened suggesting that wounds treated with the Test Article had better durability of closure. This effect is mirrored in the evaluation of wound area. Application of the Test Article daily to the wounds was found to substantially reduce the size of the wound over time. Upon microscopic evaluation, a slight decrease was noted in subacute inflammation, the degree of neovascularization, and granulomatous inflammation in the Test Article treated wounds. The results of this study demonstrate that application of the Test Article provides accelerated healing with reduced localized erythema and inflammation.

Example 2

Irritation as Measured by the Method of Lanman et al

The Lanman et al. method of irritation measurement was conducted with a cream of the invention ("Test Cream"). The objective of this study was to compare the relative cumulative irritation potential of topically applied cream to a negative (Johnson's® Baby Oil) and a positive (0.2% v/v Sodium Lauryl Sulfate) control following repetitive daily applications to the skin of normal healthy, adult volunteers. This was a single center, test site randomized, clinical trial designed to evaluate the relative cumulative irritation potential of these test articles. The compositions used were the Test Cream, Johnson's® Baby Oil and 0.2% Sodium Lauryl Sulfate (v/v in DI water). These were rubbed in to the upper back between the left and right infra-scapular areas and then covered with a blank semi-occlusive patch. Application sites were randomized as to their position on the subjects' backs to eliminate test site bias. Products were rubbed in and blank semi-occlusive patches were applied to the same sites every day for twenty-one (21) consecutive days for a total of 21 applications. Each patch was worn for approximately 24 hours, removed under clinical supervision and the test sites evaluated approximately 10 minutes following patch removal. Briefly, under semi-occlusive conditions and for up to 21 days, the data revealed that Test Cream was very well tolerated (non-irritating) and its tolerability was comparable to Johnson's Baby Oil (Negative Control).

Example 3

Sensitization

The ISO 10993-10: 2002 method was used to evaluate the allergenic potential or sensitizing capacity of a foam formulation of the invention ("Test Foam"), by screening of contact allergens in guinea pigs and extrapolating the results to humans. In the Induction Phase, ten test guinea pigs were patched with the Test Foam and 5 guinea pigs were patched with the negative control article, removed after at least 6 hour exposure. After a 24-hour rest period, each site was observed for erythema and edema. The procedure was repeated 3 times per week for 3 weeks. In the Challenge Phase, following a 2 week rest period, the animals were topically patched again, removed after at least 6 hours of exposure. Dermal patch sites were observed for erythema and edema 24 and 48 hours after patch removal. Each animal was assessed for a sensitization response and test results were based upon incidence and severity of the sensitization reaction.

None of the animals showed abnormal clinical signs during the test period. There was no irritation observed on the Test Foam and control animals during the induction phase. The dermal response incidence was 0%. None of the test animals challenged with the Test Foam was observed with a sensitization response at any time point, indicating a 0% incidence. The severity was calculated as 0 at each time point. The incidence of dermal response to repeat patch sensitization testing for the Test Foam was zero in the study demonstrating that the Test Foam does not cause dermal sensitization.

Example 4

Comedogenicity

Using the method for measuring comedogenicity detailed above, a composition of the invention and a negative control produced significantly less microcomedones than a positive control (P=0.003 and P=0.037, respectively) and the number of microcomedones at the sites treated with the composition was not significantly different from the number of microcomedones observed at the negative control sites.

Example 5

Antibacterial Effect

Twenty subjects were evaluated, ten subjects per each of the challenge species. Upon completion of a 7-day product restriction period, a trained technician applied the test formulation to the skin of one randomly assigned forearm. The subjects' other forearms served as untreated controls and received no test formulation. Four sites were delineated on the skin of each forearm and, 10 minutes following the product application procedure, the sites were exposed to the randomly assigned challenge suspension for contact times of 5 minutes, 10 minutes, 20 minutes, and 40 minutes and then sampled. Contaminated sites were not occluded, but subjects were sequestered for the duration of the evaluation.

The 7 days prior to the test portion of the study constituted the pre-test period. During this time, subjects avoided the use of medicated soaps, lotions, deodorants and shampoos, as well as skin contact with solvents, detergents, acids and bases, or any other products known to affect the normal microbial populations of the skin. Subjects were supplied a personal hygiene kit containing non-medicated soap, shampoo, lotion, and rubber gloves to be worn when contact with antimicrobials, solvents, detergents, acids, or bases cannot be avoided. Subjects were instructed to use the contents of this kit exclusively during their participation in the study. Subjects also avoided using UV tanning beds or sunbathing, and swimming or bathing in biocide-treated pools or hot tubs.

*Escherichia coli* (ATCC #11229) and *Staphylococcus aureus aureus* MRSA (ATCC #33593) were used to challenge the efficacy of the test formulation.

Approximately 48 hours prior to initiating the study, sterile tubes of Tryptic Soy Broth (TSB) were inoculated from cryogenic stock cultures or lyophilized vials containing *E. coli* and *Staph. aureus* MRSA. The microorganism cultures were incubated at 30°±2° C. for approximately 24 hours. Approximately 24 hours prior to initiating the study, the broth cultures were inoculated onto the surface of Tryptic Soy Agar (TSA) and incubated at 30°±2° C. for approximately 24 hours. Immediately prior to initiating the test procedure, suspensions of bacteria were prepared by transferring growth from the cultures on TSA into test tubes containing sterile Phosphate Buffer Solution (PBS). Suspension concentrations of approximately $1.0 \times 10^9$ CFU/mL were prepared, determined on the basis of turbidity. Serial dilutions of the challenge suspension were made in PBS to achieve a final challenge inoculum of approximately $1.0 \times 10^7$ CFU/mL. The final challenge inoculum was assayed for number of organisms at the beginning and at the end of the use period.

The left or right forearm was randomized to treatment with the test formulation, and the remaining forearm served as the untreated control. Following demarcation (see below), the four test sites on the skin of each forearm were assigned randomly and bilaterally to post-treatment sample times. Prior to sampling, the subjects were questioned regarding adherence to the protocol. Subjects were examined physically to ensure no evidence of injury was present on the skin of the forearms. The skin of the forearms was rinsed with 70% isopropyl alcohol (IPA) and allowed to air-dry. A technician selected and marked with an indelible ink marker four test sites on the volar surface of each forearm within a 2 inch by 7 inch area. The sites were spaced uniformly, starting sequentially (one through four) from the elbow moving distally toward the wrist, and the ink was allowed to dry thoroughly before continuing. 1.0 mL of the test formulation was then applied to all four sites on the randomly-assigned forearm and a gloved hand was used to distribute the product evenly over all test sites. Any test formulation that dripped to the underside of the arm was wiped with a paper towel. The test sites on forearms assigned as untreated control were not treated with test formulation.

10 minutes±1 minute following application of test formulation (or following the initial decontamination of the untreated control), the four test sites were exposed to 10 microliter of the challenge suspension of *E. coli* or *Staph. aureus* MRSA. Following 40 minute±1 minute exposure, 20 minute±1 minute exposure, 10 minute±1 minute exposure, and 5 minute±1 minute exposures, individual sites were sampled using the Cylinder Sampling Technique and then decontaminated with 70% IPA.

The cylinder sampling technique was performed as follows:

At the designated time, a sterile cylinder with an inside area of 3.46 cm2 was held firmly onto the test site to be sampled. 2.5 mL of sterile Stripping Suspending Fluid with appropriate product neutralizers (SSF++) was instilled into the cylinder, and the skin area inside the cylinder massaged in a circumferential manner for 1 minute with a sterile rubber policeman.

The 2.5 mL of SSF++ was removed with a pipette and transferred to a sterile test tube. A second 2.5 mL aliquot of SSF++ was instilled into the cylinder, and the skin area again massaged for 1 minute with a rubber policeman.

The second 2.5 mL aliquot was pooled in the test tube with the first aliquot.

Subjects were not allowed to leave the laboratory for any reason once the testing began. Additionally, subjects were required to wear protective garments and not touch their clothing, faces, or any other body parts with their forearms during the test period. On completion of testing, subjects were required to perform a I-minute rinse of their forearms with 70% ethanol and an air dry, followed by a supervised 4-minute wash with a 4% chlorhexidine gluconate solution. A topical antibiotic ointment was applied to the forearms following the decontamination procedure.

Duplicate spiral plates or duplicate spread plates were prepared from cylinder samples ($10°$ dilution) on MacConkey Agar (MAC) for *Escherichia coli* (ATCC #11229) and Hardy Chrom *Staph aureus* (CHROM) for *Staphylococcus aureus* MRSA strain (ATCC #33593). These were incubated at 30°±2° C. for approximately 48 hours and at 35°±2° C. for approximately 24 hours, respectively, or until sufficient growth was observed. Colonies were counted and data recorded using the Q-Count plate counting system or equivalent.

Publications and references, including but not limited to patents and patent applications, cited in this specification are herein incorporated by reference in their entirety in the entire portion cited as if each individual publication or reference were specifically and individually indicated to be incorporated by reference herein as being fully set forth. Any patent application to which this application claims priority is also incorporated by reference herein in the manner described above for publications and references.

While this invention has been described with an emphasis upon preferred embodiments, it will be obvious to those of ordinary skill in the art that variations in the preferred devices and methods may be used and that it is intended that the invention may be practiced otherwise than as specifically described herein. Accordingly, this invention includes all modifications encompassed within the spirit and scope of the invention as defined by the claims that follow.

What is claimed is:

1. A method of accelerating wound closure in a mammalian subject, the method comprising:
    administering topically an effective amount of a water-based formulation to a wound that is selected from the group consisting of incisions, abrasions, lacerations, penetration wounds, burns, ulcerations, surgical wounds, and piercing wounds, the water-based formulation comprising:
    an emollient comprising a silicone oil or a petrolatum,
    a fatty acid comprising stearic acid,
    one or more humectants comprising one or more of a glycerol and a propylene glycol,
    one or more emulsifying agents comprising polysorbate 20,
    one or more hydrophilic polymers selected from the group consisting of: polyethylene glycol, starch, cellulose, and carbomers, and
    water,
    wherein the water-based formulation is formulated as a spray, cream, lotion, milk or foam-former, and
    wherein said administrating is for a time sufficient to substantially achieve wound closure.

2. The method of claim 1, wherein the water-based formulation is applied as a foam using a propellant.

3. The method of claim 1, wherein the water-based formulation is essentially free of C1 to C6 alcohols but not including polyols.

4. The method of claim 1, wherein the water-based formulation further comprises a preservative.

5. The method of claim 1, wherein the water-based formulation is free of preservatives.

6. The method of claim 2, wherein the water-based formulation must be shaken prior to use.

7. The method of claim 2, wherein the foam is stable at 35° C. for at least 1 min.

8. The method of claim 1, wherein the water-based formulation is non-irritating.

9. The method of claim 1, wherein the water-based formulation is non-sensitizing.

10. The method of claim 1, wherein the water-based formulation is non-comedogenic.

11. The method of claim 1, wherein the water-based formulation comprises, by weight % of the composition:
    the one or more hydrophilic polymers in an amount in the range of 1.0-3.0%;
    stearic acid in an amount in the range of 5.0-8.0%;
    propylene glycol in an amount in the range of 4.0-7.0%;
    glycerol in an amount in the range of 1.0-2.0%;
    dimethicone in an amount in the range of 0.5-5.5%;
    triethanolamine in an amount in the range of 0.1-3.0%;
    polysorbate 20 in an amount in the range of 1.3-5.0%;
    preservative in an amount in the range of 0.0-2.0%; and
    water.

12. The method according to claim 1, wherein the water-based formulation comprises:
    0. 5 to 5 weight % of the emollient comprising silicone oil, and
    2 to 10 weight % of fatty acid comprising stearic acid.

13. The method according to claim 1, wherein the water-based formulation further comprises one or more titrants selected from a group consisting of triethanolamine, NaOH, citrate and phosphate.

14. The method according to claim 1, wherein the administering comprises administering topically the water-based formulation two to three times a day to the wound in an amount of 1 to 5 mg/cm$^2$.

15. The method of claim 1, wherein the administering results in the reduction in the incidence of erythema and/or edema in the wound.

16. The method of claim 1, wherein the silicone oil is polydimethylsiloxane.

17. The method of claim 1, wherein the water-based formulation further comprises one or more humectants selected from a group consisting of polyols, excluding glycerol and propylene glycol, polydextrose and lactic acid.

18. The method of claim 1, wherein the water-based formulation further comprises one or more emulsifying agents selected from a group consisting of sorbital fatty acid esters, octyl glucosides and pegylated lipids.

19. The method of claim 1, wherein the wound extends the full thickness of the skin.

20. The method of claim 1, wherein the water-based formulation does not contain an active anti-microbial ingredient.

21. The method of claim 1, wherein the water-based formulation consists of:
    the emollient comprising the silicone or the petrolatum;
    the fatty acid comprising stearic acid;
    the one or more humectants comprising one or more of a glycerol and polypropylene glycol;
    the one or more emulsifying agents comprising polysorbate 20;
    the one or more hydrophilic polymers selected from the group consisting of: polyethylene glycol, starch, cellulose, and carbomers;
    one or more titrants; and
    water.

22. The method of claim 1, wherein the water-based formulation consists of:
    the emollient comprising the silicone or the petrolatum;
    the fatty acid comprising stearic acid;
    the one or more humectants comprising one or more of a glycerol and polypropylene glycol;
    the one or more emulsifying agents comprising polysorbate 20;
    the one or more hydrophilic polymers selected from the group consisting of: polyethylene glycol, starch, cellulose, and carbomers;
    one or more titrants;
    one or more preservatives; and
    water.

23. The method of claim 1, wherein the water-based formulation consists of:

the emollient comprising the silicone or the petrolatum;
the fatty acid comprising stearic acid;
the one or more humectants comprising one or more of a glycerol and polypropylene glycol;
the one or more emulsifying agents comprising polysorbate 20;
the one or more hydrophilic polymers selected from the group consisting of: polyethylene glycol, starch, cellulose, and carbomers;
one or more titrants;
an active agent other than a microbial agent; and
water.

24. The method of claim 1, wherein the water-based formulation consists of:
the emollient comprising the silicone or the petrolatum;
the fatty acid comprising stearic acid;
the one or more humectants comprising one or more of a glycerol and polypropylene glycol;
the one or more emulsifying agents comprising polysorbate 20;
the one or more hydrophilic polymers selected from the group consisting of: polyethylene glycol, starch, cellulose, and carbomers;
one or more titrants;
an active agent other than a microbial agent;
one or more preservatives; and
water.

25. The method of claim 1, wherein the water-based formulation consists of:
the emollient comprising the silicone or the petrolatum;
the fatty acid comprising stearic acid;
the one or more humectants comprising one or more of a glycerol and polypropylene glycol;
the one or more emulsifying agents comprising polysorbate 20;
the one or more hydrophilic polymers selected from the group consisting of: polyethylene glycol, starch, cellulose, and carbomers;
one or more preservatives; and
water.

26. The method of claim 1, wherein the water-based formulation consists of:
the emollient comprising the silicone or the petrolatum;
the fatty acid comprising stearic acid;
the one or more humectants comprising one or more of a glycerol and polypropylene glycol;
the one or more emulsifying agents comprising polysorbate 20;
the one or more hydrophilic polymers selected from the group consisting of: polyethylene glycol, starch, cellulose, and carbomers;
an active agent other than a microbial agent; and
water.

* * * * *